United States Patent
Zhu

(10) Patent No.: US 6,564,082 B2
(45) Date of Patent: May 13, 2003

(54) METHOD FOR INCREMENTAL FIELD-OF-VIEW-MR IMAGING

(75) Inventor: Yudong Zhu, Clifton Park, NY (US)

(73) Assignee: General Electric Company, Niskayuna, NY (US)

(*) Notice: Subject to any disclaimer, the term of this patent is extended or adjusted under 35 U.S.C. 154(b) by 37 days.

(21) Appl. No.: 09/838,635

(22) Filed: Apr. 19, 2001

(65) Prior Publication Data

US 2003/0004408 A1 Jan. 2, 2003

(51) Int. Cl.[7] .................................................. A61B 5/05
(52) U.S. Cl. ..................................................... 600/410
(58) Field of Search ................................. 600/410, 409, 600/407, 408, 436, 414; 324/306, 307, 209; 476/173

(56) References Cited

U.S. PATENT DOCUMENTS

| | | | |
|---|---|---|---|
| 5,167,232 A | | 12/1992 | Parker et al. ............. 128/653.3 |
| 5,298,862 A | * | 3/1994 | Hennig ........................ 324/307 |
| 5,339,035 A | * | 8/1994 | Schneider et al. .......... 324/309 |
| 5,423,315 A | | 6/1995 | Margosian et al. ...... 128/653.2 |
| 5,483,158 A | * | 1/1996 | van Heteren et al. ....... 324/318 |
| 5,517,118 A | * | 5/1996 | Crowley et al. ............ 324/309 |
| 5,617,861 A | * | 4/1997 | Ross et al. .................. 600/410 |
| 6,037,771 A | * | 3/2000 | Liu et al. .................... 324/309 |
| 6,043,654 A | * | 3/2000 | Liu et al. .................... 324/306 |
| 6,144,873 A | * | 11/2000 | Madore et al. ............. 324/309 |
| 6,181,137 B1 | * | 1/2001 | Havens et al. .............. 324/319 |
| 6,289,232 B1 | * | 9/2001 | Jakob et al. ................ 324/307 |
| 6,400,151 B1 | * | 6/2002 | Haase et al. ................ 324/307 |

OTHER PUBLICATIONS

Daniel K. Sodickson, WJ. Manning., "Simultaneous Acquisition of Spatial Harmonics (Smash): Fast Imaging With Radiofrequency Coil Arrays", MRM 38:591–603 (1997).

Klaas P. Pruessmann, M. Weiger, MB Scheiddeger, P. Boesiger, "Sense: Sensitivity Encoding for Fast MRI", Institute of Biomedical Engineering and Medical Informatics, Univ. of Zurich and Swiss Federal Institute of Tech. Zurich, Switzerland, Jul. 9, 1999.

Ingrid Daubechies, "The Wavelet Transform, Time–Frequency Localization and Signal Analysis", IEEE Transactions of Information Theory, vol., 36, No. 5, Sep. 1990.

* cited by examiner

Primary Examiner—Teresa Walberg
Assistant Examiner—Daniel Robinson
(74) Attorney, Agent, or Firm—Jean K. Testa; Patrick K. Patnode

(57) ABSTRACT

A method for producing an image of a volume of interest using a Magnetic Resonance Imaging (MRI) system comprising the steps of acquiring a plurality of under-sampled Magnetic Resonance (MR) data sets for a plurality of regions of the volume of interest along an axis of translation within the MRI system and reconstructing the image of the volume of interest using the respective under-sampled MR data sets.

22 Claims, 5 Drawing Sheets

$$A = \begin{bmatrix} w(z+(-R-\alpha)\Delta_z) & w(z+(-R+1-\alpha)\Delta_z) & \cdots & w(z+(+R-\alpha)\Delta_z) \\ w(z+(-R-\alpha)\Delta_z - P/\Delta_{kz})e^{-j2\pi\varepsilon^P} & w(z+(-R+1-\alpha)\Delta_z - P/\Delta_{kz})e^{-j2\pi\varepsilon^P} & \cdots & w(z+(+R-\alpha)\Delta_z - P/\Delta_{kz})e^{-j2\pi\varepsilon^P} \\ \cdots & & & \\ w(z+(-R-\alpha)\Delta_z - 1/\Delta_{kz})e^{-j2\pi\varepsilon} & w(z+(-R+1-\alpha)\Delta_z - 1/\Delta_{kz})e^{-j2\pi\varepsilon} & \cdots & w(z+(+R-\alpha)\Delta_z - 1/\Delta_{kz})e^{-j2\pi\varepsilon} \\ w(z+(-R-\alpha)\Delta_z + 1/\Delta_{kz})e^{+j2\pi\varepsilon} & w(z+(-R+1-\alpha)\Delta_z + 1/\Delta_{kz})e^{+j2\pi\varepsilon} & \cdots & w(z+(+R-\alpha)\Delta_z + 1/\Delta_{kz})e^{+j2\pi\varepsilon} \\ \cdots & & & \\ w(z+(-R-\alpha)\Delta_z + P/\Delta_{kz})e^{+j2\pi\varepsilon^P} & w(z+(-R+1-\alpha)\Delta_z + P/\Delta_{kz})e^{+j2\pi\varepsilon^P} & \cdots & w(z+(+R-\alpha)\Delta_z + P/\Delta_{kz})e^{+j2\pi\varepsilon^P} \end{bmatrix}$$

*Figure 6*

METHOD FOR INCREMENTAL FIELD-OF-VIEW-MR IMAGING

BACKGROUND OF THE INVENTION

This invention relates generally to medical imaging. More particularly, this invention relates to the acquisition of magnetic resonance signals and reconstruction of images from samples of the acquired signals using a Magnetic Resonance Imaging (MRI) system.

Generally, imaging using a MRI system involves imaging a volume of interest in a MRI scanner's usable volume. The usable volume is defined as a contiguous area inside the patient bore of a Magnetic Resonance scanner and it can be rather limited in size. Typically, when the usable volume fails to cover an extended object, a method for examining the whole volume containing the object employs repeated executions of positioning and imaging a fraction of the whole volume within the scanner's usable volume. A subsequent assembling operation then assembles or "stitches" the regional images together to produce a final image of the whole volume of interest. Such an approach is typically challenged by the "stitching" artifact issue in which resulting final images often suffer from distinctive artifacts at the boundaries of the "stitched" pieces. Existing techniques achieve correct combination of regional images through full spatial encoding along patient table motion direction. They minimize "stitching" artifacts by using slab selection profiles that are as rectangular as possible, and/or discarding image data near the boundaries. As a result, these techniques tend to be inflexible, require prolonged radio frequency (RF) excitation, and involve considerable acquisition efficiency degradation.

What is needed is an effective and efficient method for producing an image of a volume of interest using a MRI system, particularly with the volume of interest that extends beyond the usable volume of the MRI system. What is further needed is a method for acquiring and reconstructing, in an "incremental field of view" fashion, data sets of a volume of interest using a MRI system that relaxes the requirements of slab selection profile and spatial encoding execution.

BRIEF SUMMARY OF THE INVENTION

A method for producing an image of a volume of interest using a Magnetic Resonance Imaging (MRI) system comprising the steps of acquiring a plurality of under-sampled Magnetic Resonance (MR) data sets for a plurality of regions of the volume of interest along an axis of translation within the MRI system and reconstructing the image of the volume of interest using the respective under-sampled MR data sets.

BRIEF DESCRIPTION OF THE DRAWINGS

The features and advantages of the present invention will become apparent from the following detailed description of the invention when read with the accompanying drawings in which:

FIG. 6 illustrates a matrix useful in deriving the reconstruction weighting function exemplified by FIG. 5; and, FIG. 7 graphically illustrates a k-space sampling grid useful in embodiments of the present invention.

DETAILED DESCRIPTION OF THE PREFERRED EMBODIMENT

Figure 1:
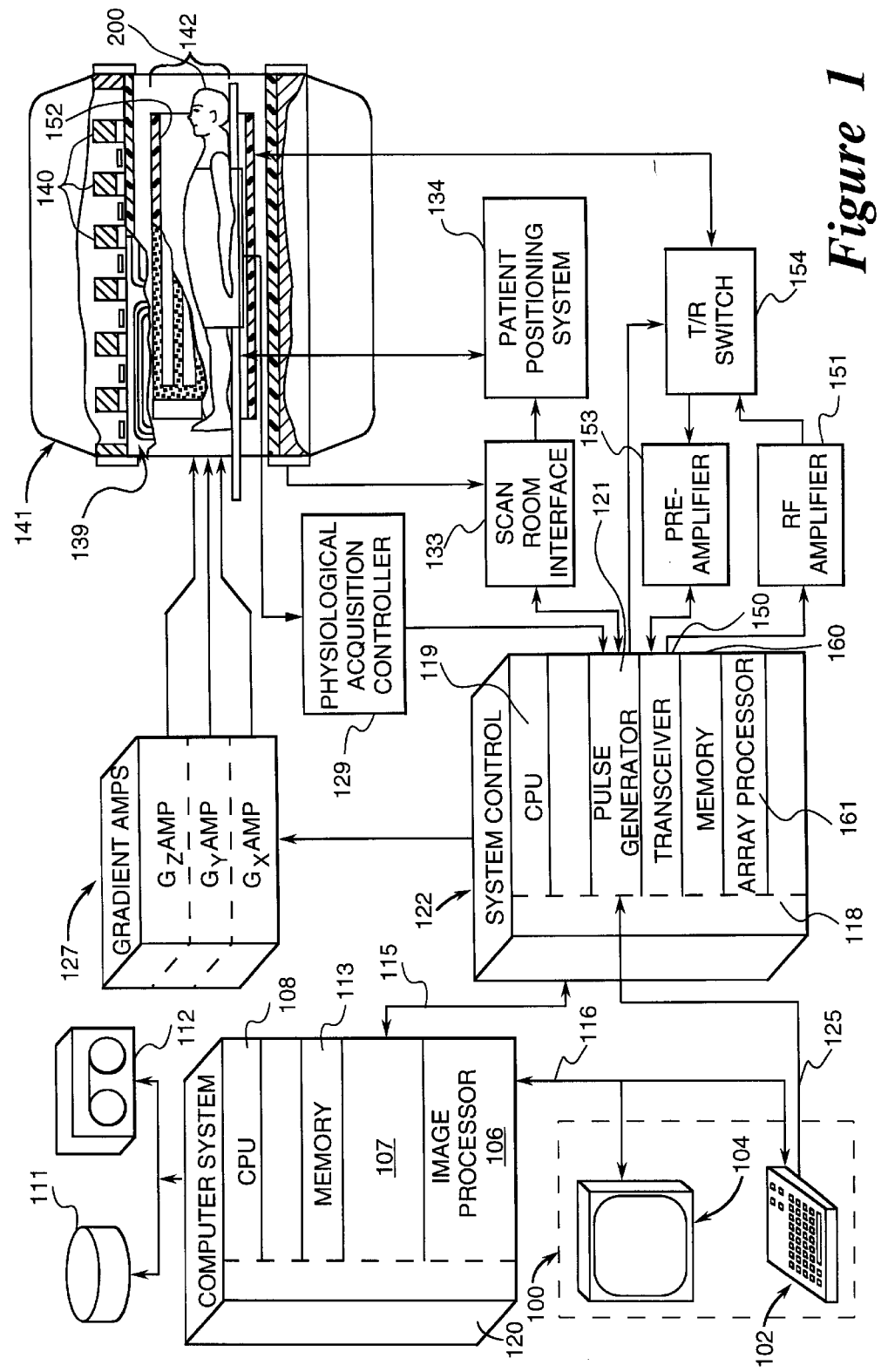
FIG. 1 illustrates a simplified block diagram of a Magnetic Resonance Imaging system to which embodiments of the present invention are useful.

FIG. 1 illustrates a simplified block diagram of a system for producing images in accordance with embodiments of the present invention. In an embodiment, the system is an MR imaging system which incorporates the present invention. The MR system could be, for example, a GE-Signa MR scanner available from GE Medical Systems, Inc., which is adapted to perform the method of the present invention, although other systems could be used as well.

The operation of the MR system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108, and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data that indicate the timing, strength, and shape of the radio frequency (RF) pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives subject data from a physiological acquisition controller 129 that receives signals from a number of different sensors connected to the subject 200, such as ECG signals from electrodes or respiratory signals from a bellows. And finally, the pulse generator module 121 connects to a scan room interface circuit 133 which receives signals from various sensors associated with the condition of the subject 200 and the magnet system. It is also through the scan room interface circuit 133 that a positioning device 134 receives commands to move the subject 200 to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. Volume 142 is shown as the area within magnet assembly 141 for receiving subject 200 and includes a patient bore. As used herein, the usable volume of a MRI scanner is defined generally as the volume within volume 142 that is a contiguous area inside the patient bore where homogeneity of main, gradient and RF fields are within known, acceptable ranges for imaging. A transceiver module 150 in the system control 122 produces pulses that are amplified by an RF amplifier 151 and coupled to the RF coil 152 by a transmit/receive switch 154. The resulting signals radiated by the excited nuclei in the subject 200 may be sensed by the same RF coil 152 and coupled through the transmit/receive switch 154 to a preamplifier 153. The amplified MR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode. It is to be appreciated that RF coil 152 is configured to be operable for MRI scanning as described below, in which a subject is translated on a positioning device along the z-axis. As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that is programmed to perform a sequel to provide an output in response to given input signals.

The MR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. These image data are conveyed through the serial link 115 to the computer system 107 where they are stored in the disk memory 111. In response to commands received from the operator console 100, these image data may be archived on the tape drive 112, or they may be further processed by the image processor 106 and conveyed to the operator console 100 and presented on the display 104. As will be discussed with reference to embodiments below, further processing is performed by the image processor 106 that includes reconstructing acquired MR image data according to embodiments described below.

In an embodiment of the present invention, a method for producing an image of a volume of interest using a Magnetic Resonance Imaging (MRI) system comprises the steps of acquiring a plurality of under-sampled MR data sets for a plurality of regions of the volume of interest along an axis of translation within the MRI system and reconstructing the image of the volume of interest using the respective under-sampled MR data sets. As used herein, a volume of interest refers to a volume within subject 200 (FIG. 1) that is being examined. The volume is either a three-dimensional (3D) volume or alternatively a two-dimensional (2D) slice. The embodiments described herein are applicable to 3D volumes and 2D slices. Generally, a volume of interest for purposes of the invention is part of the subject and may extend beyond the usable volume of the MRI scanner, for example the back or leg, and therefore requires at least two or more scans if using a conventional MRI technique.

Figure 2:
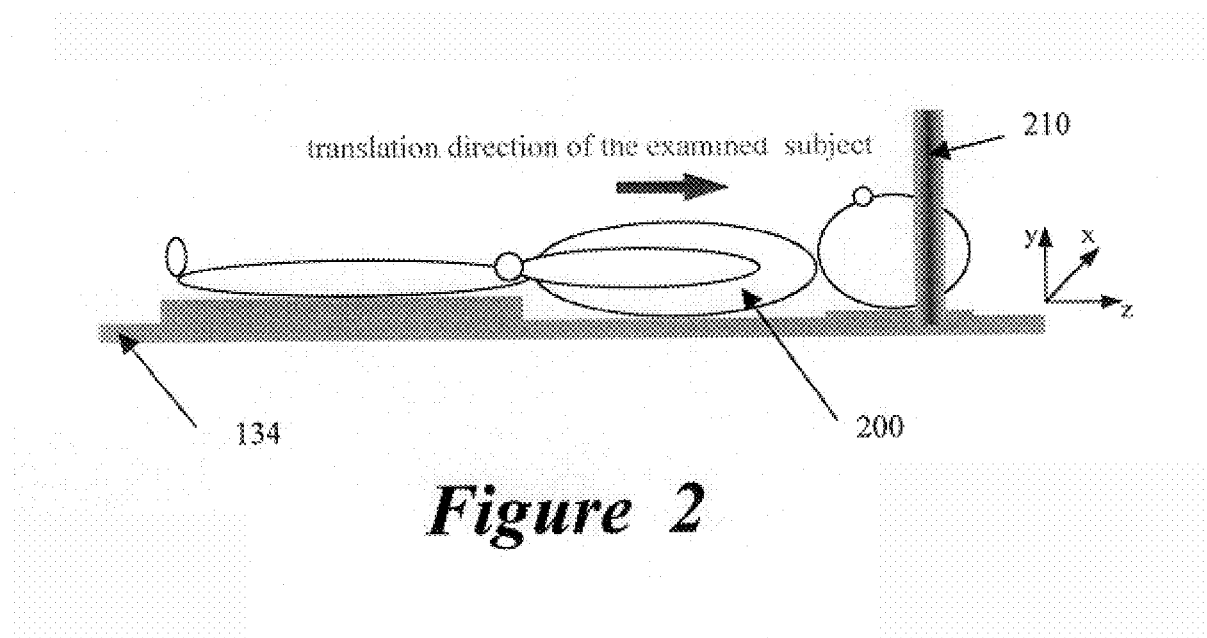
FIG. 2 is a diagram showing aspects of a MRI system for use in connection with embodiments of the invention.

Referring to FIG. 2, application of a z-direction spatially selective excitation defines an imaged region 210 within the scanner's usable volume (within volume 142 of FIG. 1), and translation of the positioning device 134 (FIGS. 1 and 2) along the z-axis and coordinated MR data acquisition effect complete coverage of the examined subject 200 with a plurality of acquired MR data sets. Each of the MR data sets is defined by imaged region 210 at a given position of translation of positioning device 134. It is to be appreciated that a MRI scanner is designed to accomplish field homogeneity subject to other important considerations such as openness, speed and cost.

Figure 4:
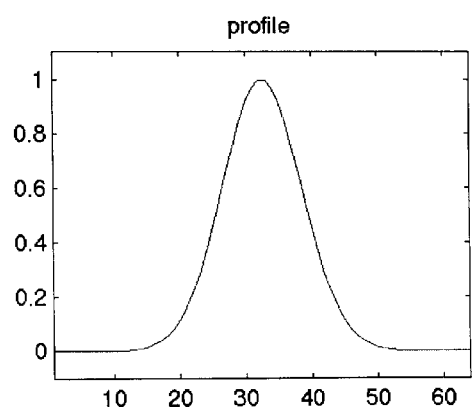
FIG. 4 graphically illustrates a RF spatially selective excitation profile useful in embodiments of the present invention.

In this embodiment of the present invention, each of the MR data sets is acquired with the presence of non-uniform spatial selectivity along the translation axis. Non-uniform spatial selectivity is achieved by appropriate design of the RF excitation pulse and/or the RF coil. In a first embodiment, the RF excitation pulse used for exciting imaged region 210 of FIG. 2 is selected to have a non-uniform spatial selectivity, e.g., a RF excitation pulse that achieves a Gaussian profile. Referring to FIG. 4, there is shown such a Gaussian profile. Alternatively in a second embodiment, the receive coil in the MRI system, such as RF coil 152 of FIG. 1, is designed to have non-uniform sensitivity so as to achieve a desired spatial selectivity. Examples of RF coils having non-uniform sensitivity include surface coils and conventional birdcage coils that are adapted for the present imaging technique. The resulting non-uniform spatial selectivity achieved by either a non-uniform excitation pulse or a non-uniform coil sensitivity result in MR data that have additional spatial information embedded in the regional images each obtained at a position along the translation axis.

Figure 3:
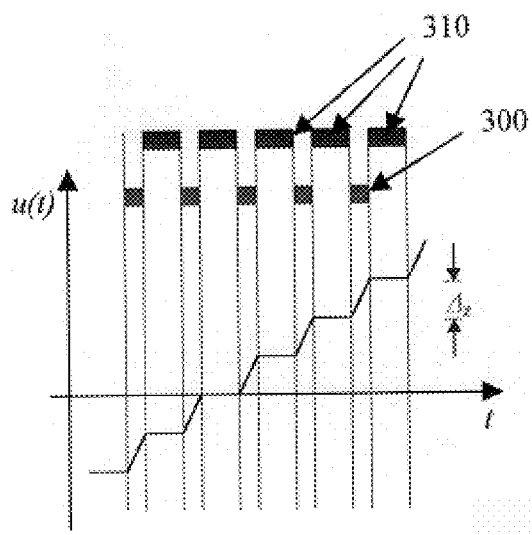
FIG. 3 graphically illustrates a sequence of stepped translations and image acquisitions useful in embodiments of the present invention.

Referring further to FIG. 2, the translation direction is shown as being along the z-direction consistent with typical MRI systems that translate a subject along the z-axis. Referring to FIG. 3, stepped translation of positioning device 134 (FIG. 2) as a function of time is shown as u(t) and image acquisition intervals 310 are shown occurring after each stepped translation of the positioning device.

As used herein, the term "under-sampled" refers to the condition in which a given MR data set is the result of a k-space sampling with density along one or more k axis substantially lower than what is normally required by an aliasing-free scan.

Reconstruction of the image of the volume of interest using the under-sampled MR data sets is performed by weighting and summing aliased regional images in a manner that substantially eliminates aliasing in the image of the full volume of interest. Reconstruction methods useful in embodiments of the present invention are derived as follows.

Suppose w(z) represents amplitude/phase effects of spatial selectivity due to RF excitation selectivity and/or receiver coil sensitivity. Ignoring relaxations, motion and coupling effects, data acquired when an imaged object is displaced along z by u (through translation of the positioning device 134 (FIG. 1)) as samples of $S_u(k_x,k_y,k_z)$, the Fourier transform of $M(x,y,z-u)w(z)$:

$$S_u(k_x,k_y,k_z)=\int\int\int M(x,y,z-u)w(z)e^{-j2\pi(k_xx+k_yy+k_zz)}dxdydz \quad (1)$$

where M(x,y,z) denotes what transverse magnetization an ideal non-selective excitation would induce if the object should be at u=0.

Figure 7:
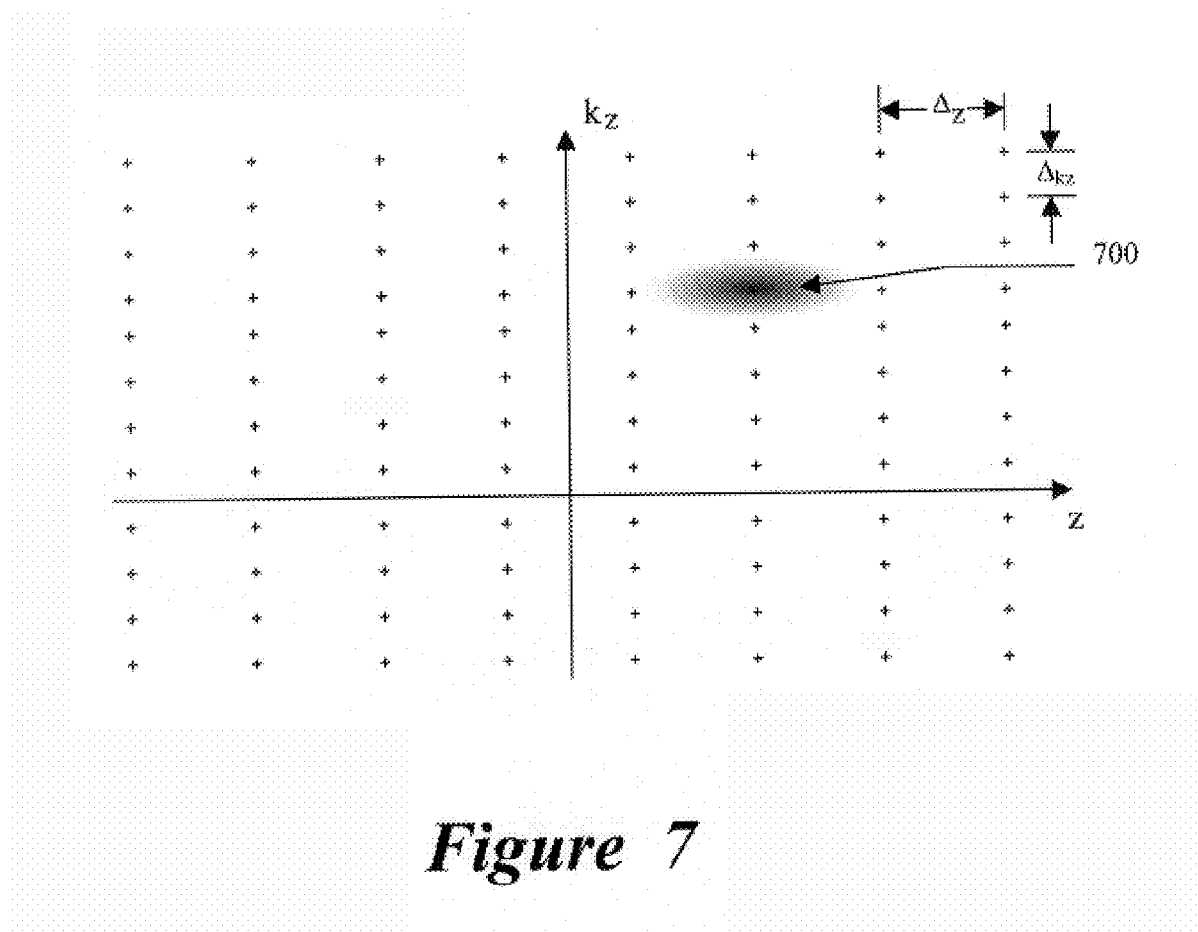

As Equation 1 and its transformed form (Parseval's theorem) indicate, the MR signal samples each explores information of M(x,y,z) in a localized space-frequency neighborhood where the energies of w(z+u) and FT{w*(z) exp(j2π($k_x$x+$k_y$y+$k_z$z))} are concentrated (FT=Fourier transform and *=complex conjugate). This leads to a concept of space-frequency domain sampling, a generalization to conventional MRI's concept of k space sampling (i.e., frequency domain sampling). For Equation 1 in particular, a z–$k_z$ plane sampling/coverage perspective is relevant: sensitivity profile w determines the shape of the space-frequency neighborhood, and positioning device translation and z-gradient spatial encoding jointly define z–$k_z$ traversing and sampling. FIG. 7 illustrates a rectangular z–$k_z$ sampling grid that is realized with even $k_z$ sampling and constant positioning device stepping: $k_z$=(m–ε)$\Delta_{kz}$ and u=(n–α)$\Delta_z$ (0≤ε,α<1 accommodate offsets). The localizd space-frequency neighborhood is illustrated at 700.

For this z–$k_z$ sampling, Equation 1 is rewritten as:

$$S_n(k_x, k_y, (m-\epsilon)\Delta_{kz}) = e^{-j2\pi(m-\epsilon)\Delta_{kz}(n-\alpha)\Delta_z} \int f_{k_x,k_y}(z) g_{m,n}^*(z) dz \quad (2)$$

where $$f_{k_x,k_y}(z) = e^{j2\epsilon\pi\Delta_{kz}} \int\int M(x,y,z) e^{-j2\pi(k_x x + k_y y)} dx dy \text{ and}$$

$$g_{m,n}(z) = e^{j2\pi m \Delta_{kz} z} w(z + n\Delta_z).$$

Developments based on the known frame theory show that if {$g_{m,n}$} a family of weighted Fourier harmonics, constitutes a frame, then M(x,y,z) may be reconstructed substantially without error as:

$$M(x, y, z) = \sum_n M_n(x, y, z) h(z + (n - \alpha)\Delta_z) \quad (3)$$

where h(z) is a reconstruction weighting function that is pre-derived from $\Delta_z$, $\Delta_{kz}$, and w(z), and regional image $M_n$(x,y,z) is computed as:

$$M_n(x, y, z) = \sum_m \left( \int\int S_n(k_x, k_y, (m-\varepsilon)\Delta_{kz}) e^{j2\pi(k_x x + k_y y)} dk_x dk_y \right) \quad (4)$$

$$e^{j2\pi(m-\varepsilon)\Delta_{kz}(z+(n-\alpha)\Delta_z)}$$

Let λ denote the product of $\Delta_{kz}$ and $\Delta_z$. In an example case where w(z) is Gaussian, {$g_{m,n}$} constitutes a frame when λ<1.

In further embodiments, Equations 3 and 4 are extended to accommodate w's that have x- or y-dependency, leading to consequent x- or y-dependency of the pre-derived h's. A more significant extension lies in the fact that x and y may be further similarly treated (stepped translation in 3 dimensions).

The space-frequency perspective leads to one key insight on $k_z$ sampling density: $\Delta_{kz}$<1/$\Delta_z$ (or equivalently, λ<1) becomes the requirement for gradient-driven z-direction spatial encoding, which may represent a significant relaxation compared to conventional MRI targeting an identical spatial resolution. This is because while the present imaging method's z-gradient must effect the same extent of $k_z$ traversing, sampling density along $k_z$ may be reduced (i.e., spacing between samples may be increased): from a value upper-bounded by 1/(width of spatial selectivity profile) to a value upper-bounded by 1/$\Delta_z$. In the example case of Gaussian sensitivity profile, $\Delta_{kz}$<1/$\Delta_z$ is a sufficient and necessary condition for resolving M(x,y,z) without aliasing.

Equations 3 and 4 define a reconstruction method for M(x,y,z) given z–$k_z$ plane sampling and a selected h function. Reconstruction of the full FOV image in accordance with Equations 3 and 4 requires computing a simple summation of spatially weighted $M_n$(x,y,z)'s, the regional images. Reconstruction of the regional images is desirably carried out on-the-fly, each, essentially a standard Fourier transform based reconstruction, computed with fast Fourier Transform (FFT). One subtlety is that, rather than the conventional width of 1/$\Delta_{kz}$, each regional image's domain of definition along z is (–∞, +∞). Therefore, each FFT result needs to be replicated along z, as far as its corresponding weighting function extends, to form a corresponding regional image. The method of the present invention imposes no restriction on sampling along $k_x$ or $k_y$. In further embodiments, for example, Cartesian or alternatively spiral $k_x$–$k_y$ sampling are used and the results are reconstructed accordingly.

Given $\Delta_z$ and the pre-derived reconstruction weighting function h, Equations 3 and 4 allow analysis of the noise propagation from acquired MR data points to reconstructed image pixels which is useful for signal to noise ratio (SNR) optimization. In particular, with knowledge of noise variance/covariance of the MR data, an analytical expression exists that explicitly predicts noise variance/covariance of the reconstructed image as a function of z. Assuming additive white data noise with standard deviation $\sigma_{data}$ for example, the noise standard deviation of a pixel at z is expressed as:

$$\sigma_{pixel}(z) = \sigma_{data} \sqrt{\sum_n |h(z - n\Delta_z)|^2} \Big/ \sqrt{\text{total number of data points at one station}} \quad (5)$$

It follows that at the same spatial resolution and $FOV_z$ of N$\Delta_z$, when compared to a reference conventional scan (defined as one using a constant spatial selectivity of unit amplitude and gradient-driven z-encodes of 1/$FOV_z$ sample spacing), $$\frac{SNR_{iFOV}}{SNR_{reference}} = \frac{1}{\sqrt{\sum_n |h(z - n\Delta_z)|^2} \sqrt{\lambda N}} \quad (6)$$

where $SNR_{iFOV}$ refers to the signal to noise ratio in the incremental imaging methods described with reference to embodiments of the present invention. The term √λN appears in the denominator reflecting the intrinsic SNR penalty associated with a λN-fold reduction in the number of averaged noise samples. The other term in the denominator, √$\Sigma_n$|h(z–n$\Delta_z$)|², is a geometrical factor that is one main target when minimization of SNR penalty is pursued.

In the present invention, the reconstruction weighting function h(z) is pre-computed based on $\Delta_z$, $\Delta_{kz}$, and w(z). The following embodiments all target at deriving the reconstruction weighting function h(z) to additionally provide a) a measure of residual aliasing, and b) a capability to flexibly trade off integrity from aliasing for robustness against noise (i.e., to improve signal to noise ratio by controllably accepting some level of residual aliasing).

A basic method of deriving reconstruction weighting function h(z) is now described. With the z–$k_z$ plane sampling grid illustrated above, a regional image reconstructed from data collected at position l (l is the index for the position of the positioning device: position l corresponds to $u=(l-\alpha)\Delta_z$) is expressed as (x- and y-dependency suppressed for simplicity):

$$M_l(z) = \sum_p w(z + (l-\alpha)\Delta_z - p/\Delta_{kz})e^{-j2\pi\varepsilon p}M(z-p/\Delta_{kz}) \quad (7)$$

Assuming $(-R\Delta_z, +R\Delta_z)$ defines the region outside of which the magnitude of w(z) is negligible. It is noted that only at positions n−R, n−R+1, ..., n+R−1 and n+R will pick up MR signals that have contributions from spins in region $(-n\Delta_z - \Delta_z/2, -n\Delta_z + \Delta_z/2)$, and hence need be taken into account in the reconstruction of the region. Let the reconstruction be a weighted superposition of aliased images obtained at positions n−R, n−R+1, . . ., n+R−1 and n+R:

$$\sum_{l=n-R}^{n+R} h(z+(l-\alpha)\Delta_z)M_l(z) = \sum_{l=n-R}^{n+R} h(z+(l-\alpha)\Delta_z) \quad (8)$$

$$\sum_{p=-P}^{P} w(z+(l-\alpha)\Delta_z - p/\Delta_{kz})e^{-j2\pi\varepsilon p}M(z-p/\Delta_{kz})$$

where P is the minimum integer that is greater or equal to $(2R+1/2)\lambda$. For a weighted superposition of (aliased) regional images, or component-coil images, to accurately reconstruct a full-FOV image, $\Sigma_l h(z+(l-\alpha)\Delta_z)M_l(z)$ should match M(z) as closely as possible regardless of M(z)'s shape. The aliased terms in Equation 8 therefore must be substantially negligible in magnitude. This, when expressed in matrix form, translates to Ah=$e_1$, where $$h=[h(z+(-R-\alpha)\Delta_z)h(z+(-R+1-\alpha)\Delta_z) \ldots h(z+(R-\alpha)\Delta_z)]^T,$$

$$e_1=[1\ 0\ \ldots\ 0]^T,$$

and A is a matrix fully defined by $\Delta_z$, $\Delta_{kz}$ and w(z) and is shown in FIG. 6. Solving equation Ah=$e_1$ with least squares for each z location in $[0,\Delta_z)$ generates a weighting function.

In effect, for each z location, $\|Ah-e_1\|$, the norm of the difference between Ah and $e_1$, serves as a measure of residual aliasing level, and should be of substantially insignificant amplitude to ensure accurate reconstruction. Relaxing requirement on $\|Ah-e_1\|$ however, is practically desirable for robustness/SNR considerations. Rather than using a simple least squares as above, the following describes two embodiments which derive h for less signal to noise (SNR) penalty while maintaining control over reconstruction accuracy.

A first embodiment for deriving h seeks a desired balance between residual aliasing and image SNR. It is primarily applicable when reconstruction operates in a regime where $\lambda=\Delta_{kz}\Delta_z>1$ and reconstruction without aliasing is not possible. In this case, h is desirably derived to minimize $\|Ah-e_1\|+\eta\|h\|$, where $\eta$ is a weighting reflecting relative interest on maximum signal-to-noise ratio (SNR) versus minimum residual aliasing. This derivation is formulated and solved as a least squares problem.

A second embodiment for deriving h seeks to maximize SNR within the confinement of a chosen upper limit on residual aliasing level, reflecting a prioritization on imaging accuracy control. It is primarily applicable when reconstruction operates in a regime where $\lambda=\Delta_{kz}\Delta_z\leq 1$ and reconstruction without aliasing is realizable. It is known that as $\lambda$ approaches 1 or as the $z-k_z$ plane sampling neighborhood assumes an extremely elongated shape, reconstruction robustness and SNR degrades. In the case of Gaussian profile, numerical stability of a reconstruction that strives for minimum aliasing worsens drastically when $\lambda$ goes beyond 0.996. For the regime, the present embodiment formulates the derivation of h as a problem of finding the h that minimizes $\|h\|$ subject to $\|Ah-e_1\|<\tau$, where $\tau$ is a scalar representing a maximum level of tolerable residual aliasing. Singular value decomposition suggests itself as a powerful numerical tool. Let U$\Sigma$V* denote the singular value decomposition of matrix A, where U and V are orthogonal matrices and $\Sigma$ is a diagonal matrix with $\sigma_j$'s, the singular values of A, on the diagonal. A standard minimum norm solution is found by computing V$\Sigma^\dagger$U*$e_1$, where $\Sigma^\dagger$ is the result of transposing $\Sigma$ and replacing each of the non-zero $\sigma_j$'s with its reciprocal. In the present embodiment, a threshold $\rho$ is chosen, each of the $1/\sigma_j$'s in $\Sigma^\dagger$ is set zero whenever $\sigma_j \leq \rho$, and then V$\Sigma^\dagger$U*$e_1$ is computed. The result effectively minimizes image noise standard deviation for a certain residual aliasing level. The flexibility in trading off reconstruction accuracy for lower image noise is appreciated by noting the property that, if $\rho_1 \leq \rho_2$, then $\tau_1 \leq \tau_2$ but $\|h_1\| \geq \|h_2\|$. The rational behind the method include: a) the more zeros these $1/\sigma_j$'s are replaced with, the smaller the norm of V$\Sigma^\dagger$U*$e_1$, the solution for h, and typically the larger the norm of the error (residual aliasing level), and b) $\sqrt{\Sigma_n |h(z-n\Delta_z)|^2}=\|h\|$.

Finally it can be shown that a useful scaling property holds. If h(z) denotes optimum reconstruction weighting function derived for a given $\{w(z), \Delta_z \text{ and } \Delta_{kz}\}$ set using the methods described earlier, then for $\{w(\beta_z), \beta\Delta_z \text{ and } \Delta_{kz}/\beta\}$, the optimum weighting is h($\beta_z$).

Figure 5:
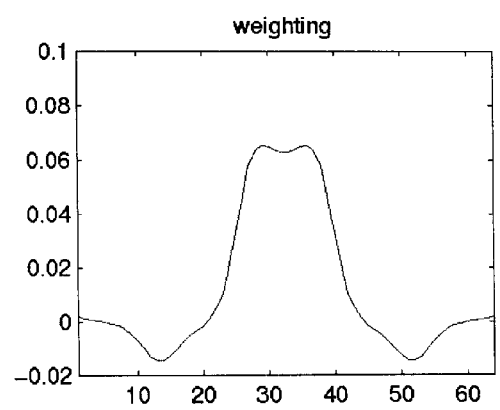
FIG. 5 graphically illustrates a reconstruction weighting function useful in embodiments of the present invention.

Referring to FIG. 5, there is shown a representative illustration of weighing h(z) are described above in Equations 3–8.

In a further embodiment, reconstruction computations using Equation (3) are evaluated on-the-fly, with each $M_n$(x, y,z) computed with fast Fourier Transform (FFT) techniques. As used herein, reconstructing "on-the-fly" refers to incrementally reconstructing an image with the evaluated Fourier transform in which the computations occur during data acquisition. Thus, reconstruction computation occurs "on-the-fly", that is it is initiated and executed during the time of data acquisition by the MR scanner.

In further embodiments, reconstruction is based on adaptations of known techniques of filling up skipped k-space lines based on synthesizing Fourier harmonics or known techniques of resolving localization ambiguities directly with coil sensitivity mapping. In a first further embodiment, reconstruction is based on filling up skipped k-space lines based on approximating Fourier harmonics with linearly combined spatial selectivity profiles and thus reconstruct a full-FOV image substantially free of aliasing artifacts. In a second further embodiment, reconstruction is processed in accordance with sensitivity encoding techniques. Such sensitivity encoding is based on resolving localization ambiguities by algebraically extracting spatial information encoded with the spatial selectivity profiles and thus reconstruct a full-FOV image substantially free of aliasing artifacts.

A further embodiment includes adapting the described embodiments for use in a conventional multi-slab volume imaging setting, in which the subject remains stationary and w(z) displaces incrementally to select respective z-slabs which are then combined to form a full volume. Thus, in this alternative embodiment, the volume of interest is fixed in space and the translation is translation of the excited location relative to the fixed volume of interest.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method for producing an image of a volume of interest using a Magnetic Resonance Imaging (MRI) system comprising:

acquiring a plurality of under-sampled Magnetic Resonance (MR) data sets for a plurality of regions of said volume of interest along an axis of translation within the MRI system; and, reconstructing said image of said volume of interest using said respective under-sampled MR data sets.

2. The method of claim 1 wherein the acquiring step uses an excitation pulse with non-uniform spatial selectivity along the translation axis.

3. The method of claim 1 wherein the acquiring step uses a receive coil with non-uniform sensitivity along the translation axis.

4. The method of claim 2 wherein said non-uniform spatially selective excitation pulse is a RF excitation pulse having a Gaussian profile.

5. The method of claim 3 wherein said receive coil with non-uniform spatial sensitivity is a surface coil.

6. The method of claim 3 wherein said receive coil with non-uniform spatial sensitivity is a birdcage coil.

7. The method of claim 1 wherein said translation is translation of said volume relative to an imaged location.

8. The method of claim 1 wherein said volume is fixed in space and said translation is translation of spatial selectivity relative to said volume.

9. The method of claim 1 wherein said axis of translation is the z-axis of the MRI system and said translation is stepped and synchronized with the acquiring step.

10. The method of claim 1 wherein the reconstructing step is performed by weighting and summing a plurality of regional images computed by said plurality of under-sampled MR data sets.

11. The method of claim 1 wherein the reconstructing step comprises the steps of:

computing a plurality of regional images from said respective under-sampled MR data sets; and, weighting and summing said plurality of regional images to produce said image of said volume of interest.

12. The method of claim 1 wherein the reconstructing step is performed incrementally during the acquiring step.

13. The method of claim 1 wherein the reconstructing step is processed in accordance with spatial harmonic synthesizing techniques.

14. The method of claim 1 wherein the reconstructing step is processed in accordance with sensitivity encoding techniques.

15. A method for producing an image of a volume of interest using a Magnetic Resonance Imaging (MRI) system comprising:

incrementing a positioning device along an axis of the MRI system through a plurality of given positions to incrementally define a plurality of respective regions within said volume of interest;

acquiring a respective under-sampled MR data set for each of said respective plurality of regions;

computing a plurality of regional images corresponding to said under-sampled MR data sets for each of said given positions; and, reconstructing said image of said volume of interest from said respective regional images.

16. The method of claim 15 wherein the acquiring step uses an excitation pulse with non-uniform spatial selectivity along the axis.

17. The method of claim 15 wherein the acquiring step uses a receive coil with non-uniform sensitivity along the axis.

18. The method of claim 16 wherein said non-uniform spatially selective excitation pulse is a RF excitation pulse having a Gaussian profile.

19. The method of claim 15 wherein the reconstructing step further comprises the steps of:

weighting and summing said plurality of regional images to produce said image of said volume of interest.

20. The method of claim 15 wherein the reconstructing step is performed incrementally during the acquiring step.

21. The method of claim 15 wherein the reconstructing step is processed in accordance with $$M(x, y, z) = \sum_n M_n(x, y, z) h(z + (n-\alpha)\Delta_z) \text{ and } M_n(x, y, z) =$$

$$\sum_m \left( \int \int S_n(k_x, k_y, (m-\varepsilon)\Delta_{kz}) e^{j2\pi(k_x x + k_y y)} dk_x dk_y \right)$$

$$e^{j2\pi(m-\varepsilon)\Delta_{kz}(z+(n-\alpha)\Delta_z)}$$

where h(z) is a reconstruction weighting function that is pre-derived from $\Delta_z$, $\Delta_{kz}$, and w(z), w(z) being a spatial selectivity.

22. The method of claim 21 wherein h(z) is derived in accordance with singular value decomposition techniques that minimize $\|h\|$ subject to $\|Ah - e_1\| < \tau$, where $\tau$ is a scalar representing a maximum level of tolerable residual aliasing.

* * * * *